US008734871B2

(12) United States Patent  
Molteni

(10) Patent No.: US 8,734,871 B2
(45) Date of Patent: May 27, 2014

(54) GLYCOLIPID FRACTION FROM CYANOBACTERIA FOR TREATMENT OF DISEASES OF THE ORAL CAVITY

(75) Inventor: Monica Molteni, Agrate Brianza (IT)

(73) Assignee: Bluegreen Biotech S.R.L., Milan (IT)

( * ) Notice: Subject to any disclaimer, the term of this patent is extended or adjusted under 35 U.S.C. 154(b) by 166 days.

(21) Appl. No.: 13/054,788

(22) PCT Filed: Jul. 24, 2009

(86) PCT No.: PCT/EP2009/059565
§ 371 (c)(1),
(2), (4) Date: Jan. 18, 2011

(87) PCT Pub. No.: WO2010/010172
PCT Pub. Date: Jan. 28, 2010

(65) Prior Publication Data
US 2011/0130351 A1    Jun. 2, 2011

(30) Foreign Application Priority Data
Jul. 25, 2008    (IT) .............................. MI2008A1370

(51) Int. Cl.
*A61K 35/66* (2006.01)
*A61K 35/74* (2006.01)

(52) U.S. Cl.
USPC ........................................................ 424/780

(58) Field of Classification Search
None
See application file for complete search history.

(56) References Cited

U.S. PATENT DOCUMENTS

| | | | | |
|---|---|---|---|---|
| 2010/0015125 A1* | 1/2010 | Crispe et al. | ................ | 424/130.1 |
| 2011/0053216 A1* | 3/2011 | Vermaas | ...................... | 435/69.1 |
| 2011/0311562 A1* | 12/2011 | Molteni | ..................... | 424/184.1 |
| 2012/0184003 A1* | 7/2012 | Chen et al. | .................... | 435/134 |

OTHER PUBLICATIONS

International Search Report for PCT/EP2009/059565 filed on Jul. 24, 2009 in the name of Bluegreen Biotech S.R.L.
Written Opinion for PCT/EP2009/059565 filed on Jul. 24, 2009 in the name of Bluegreen Biotech S.R.L.
E. B. Thorgersen et al., "Cyanobacterial LPS antagonist (CyP)—A novel and efficient inhibitor of *Escherichia coli* LPS-induced cytokine response in the pig", Molecular Immunology, 45; p. 3553-3557 (2008).
K. Jemmett et al., "A Cyanobacterial Lipopolysaccharide Antagonist Inhibits Cytokine Production Induced by *Neisseria meningitidis* in a Human Whole-Blood Model of Septicemia", Infection and Immunity, 76;7 p. 3156-3163 (2008).
A. Macagno et al., "A cyanobacterial LPS antagonist prevents endotoxin shock and blocks sustained TLR4 stimulation required for cytokine expression", The Journal of Experimental Medicine, 203;6 p. 1481-1492 (2006).

E. C. Yi et al., "Rapid isolation method for lipopolysaccharide and lipid A from Gram-negative bacteria", Analyst, 125; p. 651-656 (2000).
Q. Zhou et al., Identification of Signaling Pathways in Macrophage Exposed to *Porphyromonas gingivalis* or to Its Purified Cell Wall Components The Journal of Immunology[1], 179; p. 7777-7790 (2007).
M. Prati et al., "Biological effect of the *Planktothrix* sp. FP1 cyanobacterial extract", Toxicon, 40; p. 267-272 (2002).
Komerik, N., et al., In Vivo Killing of *Porphyromonas gingivalis* by Toluidine Blue-Mediated Photosensitization in an Animal Model, Antimicrobial Agents and Chemotherapy 2003, 47: 932-940.
Eick, S., et al., In vitro antibacterial activity of fluoroquinolones against *Porphyromonas ginvalis* strains, J. of Antimicrobial Chemotherapy 2004, 54: 553-556.
European Communication 94(3) issued for European Application No. 09781039.4 in the name of Bluegreen Biotech S.R.L. mail date: Oct. 7, 2011.
Teng Y-TA, Protective and destructive immunity in the periodontum: part 1—Innate and humoral immunity and the periodontum. J. Dent. Res. 2006, 85:198-208.
Bodet C, et al. Inflammatory responses of a macrophage/epithelial cell co-culture model to mono and mixed infections with *Porphyromonas gingivalis, Treponema denticola*, and *Tannerella forsythia*. Microbes Infection 2006, 8:27-35.
Bodet C, et al., *Porphyromonas gingivalis*-induced inflammatory mediator profile in an ex vivo human whole blood model. Clin. Exp. Immunol. 2005, 143:50-57.
Wang P-L, et al., *Porphyromonas gingivalis* lipopolysaccharide signaling in gingival fibroblasts-CD14 and toll-like receptors. Grit. Rev. Oral. Biol. Med. 2002, 13:132-142.
Shapira L, et al., Strain-dependent action of monocytes and inflammatory macrophages by lipopolysaccharide of *Porphyromonas gingivalis*. Infect. Immunity 1998: 66:2736-2742.
Saba JA, et al., Proteomic mapping of stimulus-specific signalling pathways involved in THP-1 cells exposed to *Porphyromonas gingivalis* or its purified components. J. Proteome Res. 2007, 6:2211-2221.
Wens C, et al., Leptospiral lipopolysaccharide activates cells through a TLR2-dependent mechanism. Nature 2001, 2:346-352.

(Continued)

*Primary Examiner* — Chris R Tate
(74) *Attorney, Agent, or Firm* — Steinfl & Bruno, LLP

(57) ABSTRACT

The present invention relates to the preparation and use of a glycolipid fraction from *Oscillatoria Planktothrix* sp., for the treatment and/or prevention of bacterial gum diseases primarily caused by: *Actinobacillum actinomycetemconcomitans, Porphyromonas gingivalis, Tannerella forsythia, Treponema denticola* and even more preferably by *Porphyromonas gingivalis*. Said gum diseases, in particular gingivitis and periodontitis (pyorrhea), are primarily caused by a pro-inflammatory response to components of *P. gingivalis*, leading to destruction of periodontal tissue, and are often accompanied by osteoclastogenesis (increased number of osteoclasts responsible for destruction of bone tissue), and by chronic infection.

20 Claims, 1 Drawing Sheet

(56) References Cited

OTHER PUBLICATIONS

Darveau RP, et al., *Porphyromonas gingivalis* lipopolysaccharide contains multiple lipid A species that functionally interact with both toll-like receptors 2 and 4. Infect. Immunity 2004, 72:5041-5051.

Pomati et al., The freshwater Cyanobacterium *Planktothrix* SP. FP1: Molecular Identification and Detection of Paralytic Shellfish Poisoning Toxins J. Phycol. 2000, 36:553-562.

Chomczynski P., et al., Modification of the tri-reagent procedure for isolation of RNA from polysaccharide- and proteoglycan-rich sources. Biotechniques 1995, 19: 942-945.

Macagno, A., et al., A cyanobacterial LPS antagonist prevents endotoxin shock and blocks sustained TLR4 stimulation required for cytokine expression. The Journal of Experimental Medicine 2006, 203: 1481-1492.

Yi, E., et al., Rapid isolation method for lipopolysaccharide and lipid A from Gram-negative bacteria, Analyst 2000, 125:651-656.

Zhou, Q., et al., Identification of Signaling Pathways in Macrophage Exposed to *Porphyromonas gingivalis* or to Its Purified Cell Wall Components, The Journal of Immunology 2007, 179: 7777-7790.

1—Petersen, P.E. et al. *Strengthening the Prevention of Periodontal Disease: The WHO Approach*. J Periodontol, Dec. 2005, vol. 76 (12), pp. 2187-2193.

2—Center for Disease Control and Prevention. *CDC Aims to Prevent Oral Diseases Among Older Americans*. Mar. 3, 2005, pp. 1-12.

3—American Academy of Periodontolgy. *Protecting Children's Oral Health*. May 19, 2008. Web. <http://web.archive.org/web/20080626152026/http://www.perio.org/consumer/children.htm.>.

4—MayoClinic.com. *Gingivitis: Prevention*. Jun. 23, 2008. Web. <http://web.archive.org/web/20080623090956/http://www.mayoclinic.com/health/gingivitis/DS00363/DSECTION=prevention>.

5—Medline Plus Medical Encyclopedia. *Gingivitis*. Apr. 28, 2008. Web. <http://web.archive.org/web/20080509193635/http://www.nlm.nih.gov/medlineplus/ency/arlicle/001056.htm.>.

6—Merriam-Webster. Prophylaxis. 2013. Web. <http://www.merriam-webster.com/dictionary/prophylaxis?show=0&t=1370280931 >.

7—National Institute of Dental and Craniofacial Research. *Periodontal (Gum) Disease: Causes, Symptoms, and Treatments*. Apr. 2, 2008. Web. <http://web.archive.org/web/20080705171401/http://www.nidcr.nih.gov/OralHealth/Topics/GumDiseases/PeriodontalGumDisease.htm>.

8—National Public Health Partnership. *The Language of Prevention*. 2006, Melbourne: NPHP. pp. 1-8.

\* cited by examiner

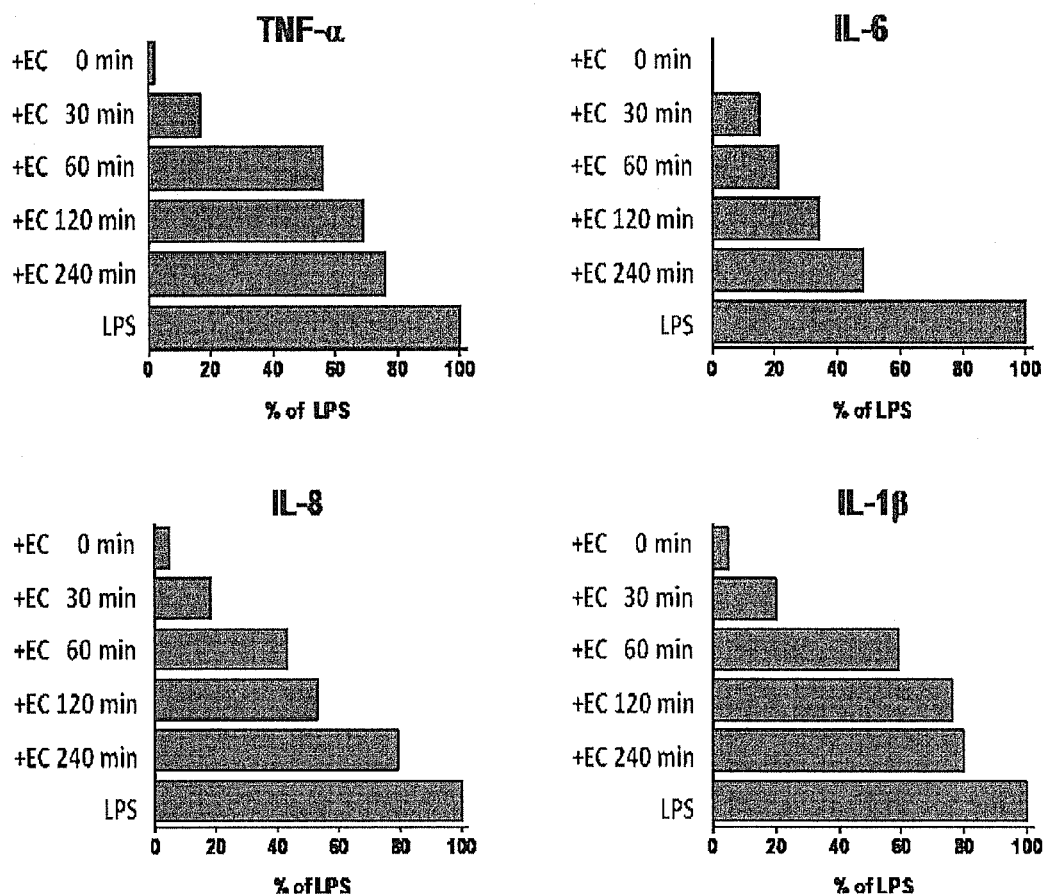

GLYCOLIPID FRACTION FROM CYANOBACTERIA FOR TREATMENT OF DISEASES OF THE ORAL CAVITY

CROSS REFERENCE TO RELATED APPLICATIONS

The present application is the US national stage of International Application PCT/EP2009/059565 filed on Jul. 24, 2009 which, in turn, claims priority to Italian Patent Application MI 2008A001370 filed on Jul. 25, 2008.

FIELD OF THE INVENTION

The present invention relates to the field of coadjuvants for oral hygiene and treatment of diseases of the oral cavity.

STATE OF THE ART

Periodontitis is a oral disease caused by some species of gram-negative bacteria. It is a chronic inflammatory disease of the oral tissue, characterized by chronic bacterial infections that cause the irreversible destruction of the tissue supporting the teeth. This is a very common disease affecting about ¾ of the adult population with various degrees of severity (1). Subgengival tissue is characterized by the presence of many bacterial species, but only few of them are responsible for the initiation and progression of periodontitis. These are 4 species of gram-negative bacteria (*Actinobacillum actinomycetemconcomitans, Porphyromonas gingivalis, Tannerella forsythia, Treponema denticola*), facultative or obligate anaerobes, which produce a number of factors that allow them to colonize the subgengival region, to resist the host immune immune system and cause tissue destruction (2-4). Among these, however, *Porphyromonas gingivalis* (*P. gingivalis*) is the bacterium most often associated with the advanced stage periodontitis. The incidence and degree of progression of the parodontal disease involves complex interactions between periodontopatic bacteria and host immune system. It has been shown that activation of host immune cells by these bacteria and their products leads to secretion of a number of pro-inflammatory mediators, such as cytokines and matrix metalloproteinases (MMPs), that modulate destruction of the periodontal tissue and also induce osteoclastogenesis (2). The lypopolisaccharide (LPS) present on the cell wall of gram-negative bacteria is the main factor that can trigger the release of pro-inflammatory mediators by immune cells which reside in the oral mucosa or are recruited during the infection process, such as monocytes, macrophages, polymorphonuclear leukocytes, dendritic cells (4-6). Professional treatment of periodontitis has been supported by the use of oral hygiene aids such as toothpaste and mouthwash, which preferably contain disinfectants or broad spectrum antibacterial agents, such as triclosan, chlorhexidine, or in some cases, antibiotics. However, according to the most recent studies, the use of disinfectants and/or antibacterial agents of this kind is not entirely advisable for several reasons, the first being certainly the apparent cellular toxicity of some compounds such as triclosan. This is a reason why their use was even banned in some countries of the European Community, and the second being that LPS (or molecules similar to LPS), the main pro-inflammatory stimulus, is not inactivated by the germicidal activity commonly present in mouthwash and/or toothpaste; then its effect as pro-inflammatory stimulus is maintained even after the eradication of bacterial infection. The third reason is that the broad spectrum antimicrobial activity has the undesirable side effect of eliminating also the "useful" or "good" microbial flora. Not least, therefore, even the use of normal protective agents for oral hygiene does not specifically eliminate the pro-inflammatory activity. Therefore, the development of preparations for oral hygiene which, in addition to eliminating the bacterial agent, contribute to specifically inhibit the associated pro-inflammatory stimulus is highly desirable in the dental field.

SUMMARY OF THE INVENTION

The present invention relates to the glycolipid fraction from *Oscillatoria Planktothrix* sp., for the treatment and/or prevention of bacterial gum disease wherein protein contamination is lower than 2% and nucleic acid contamination is lower than 5%. Etiology of the gum disease is preferably due to an infection caused by an anaerobic bacterium selected from the group comprising: *Actinobacillus actinomycetemcomitans, Porphyromonas gingivalis, Tannerella forsythia, Treponema denticola* and even preferably *Porphyromonas gingivalis*. Gum diseases are preferably gingivitis and periodontitis (pyorrhea). Further object of the invention are dental compositions comprising the above-mentioned glycolipid fraction, preferably in quantities ranging between 0.1 and 100 µg/ml, including, as ingredients and/or diluents and/or stabilizers and/or additives, compounds suitable for oral administration, and optionally one or more different active ingredients. Preferably the concentration of the active fraction is comprised between 1 and 50 µg/ml, preferably 4-20 µg/ml for paste or gel and 1-5 µg/ml for mouthwash. Another object of the invention is a process for the preparation from *Oscillatoria Planktothrix* sp. of a glycolipid fraction suitable for oral use.

BRIEF DESCRIPTION OF THE FIGURES

FIG. 1. Inhibition of the production of pro-inflammatory cytokines in the presence of cyanobacterial extract (CE) (20 µg/ml) added simultaneously at 30, 60, 120, 240 minutes after LPS from *P. gingivalis*. Panel A: TNF-α; panel B: IL-6; panel C: IL-8; panel C: IL-1β.

DETAILED DESCRIPTION OF THE INVENTION

Recently, it was shown that a glycolipid extract prepared from the cyanobacterium *Oscillatoria Planktothrix* FP1 is able to antagonize in human dendritic cells the pro-inflammatory effects triggered by TLR4 receptor LPS agonists, such as the LPS from *E. coli* and *S. abortus* equi (10). The present invention arises from a further observation that the extract also antagonises the pro-inflammatory effects of LPS from *Porphyromonas gingivalis* (*P. gingivalis*). *P. gingivalis* is the most common bacterium that is associated with periodontitis or chronic periodontitis, of which it has been shown to be the primary causative agent. In particular, the pro-inflammatory response is related to the presence of its components LPS and Fim 1, purified as described in (9). These components are currently considered as the main cause for destruction of the periodontal tissue associated with *P. gingivalis* infection, that is often associated with osteoclastogenesis (increased number of osteoclasts responsible for destruction of bone tissue) and chronic infection. The finding of the present invention is especially surprising in view of the previously shown activity toward *E. coli* and *S. abortus* equi LPS because LPS from *P. gingivalis* exerts its activity through interaction with the TLR2 receptor (7-9), whereas many bacterial LPS activate innate immunity cells through interaction with the TLR4 membrane receptor belonging to the Toll-like receptor family (TLR). Therefore, according to a first aspect, the invention relates to the *Oscillatoria Planktothrix* sp. glycolipid fraction, the isolation of which and growth conditions are described in (12) for use in prevention and/or treatment of gum disease and bacterial periodontitis.

in vitro studies on a human monocytic cell line have shown that the glycolipid fraction from *Oscillator Planktothrix* sp. is able to antagonize primarily the pro-inflammatory effects (ie the production of cytokines and pro-inflammatory chemokines) induced by LPS of *P. gingivalis*. Thus this represents a good candidate to fight gingival inflammation (gingivitis) and conditions of mild and severe inflammation of the dental alveoli (periodontitis or pyorrhea), destruction of periodontal tissue associated with chronic infection and the most severe phenomena of osteoclastogenesis that are found just as frequently in these infections. In vitro studies have also shown that cyanobacterial extracts prepared according to the invention, showing a level of protein contamination below 2% and a level of nucleic acid contamination below 5%, are not cytotoxic for mammalian cells as assessed in cytotoxic assays in cell lines as well as in PBMC isolated from human blood. It is therefore possible to claim their use for treatment of the oral cavity, both under the form of a composition for professional treatment of gingival diseases, particularly gingivitis, pyorrhea and periodontitis, and under the form of a composition to be used as adjuvant for oral hygiene, such as mouthwash, gel, paste or devices that can be chewed or dissolved in the mouth, e.g. chewing-gum or candy. The lack of cytotoxicity of the extract of the invention has been tested in cellular systems in vitro up to a concentration (100 µg/ml) that is 100-fold higher than the minimum effective concentration. The extract of the invention, prepared as described below, is odorless, colorless and tasteless: therefore it is also possible its use in food preparations that can be chewed or dissolved in the oral cavity, e.g. in the form of sugar-coated pills, chewing gum, candies or pills (also in combination with other active substances e.g. xylitol) if combined with other ingredients or components with the same characteristics. Therefore the compositions containing the extract possess the advantageous properties of lacking cytotoxicity, under the conditions described, and satisfactory organoleptic qualities. In order to improve the latter, however, the compositions may include flavoring or coloring agents and sweeteners, in small quantities.

The extract is conveniently prepared in the form of a composition suitable for oral administration and can be prepared in a more or less concentrated form as protective preparation for professional use in dental cleaning and for prevention and treatment of pyorrhea, of more severe gingivitis and in general of periodontitis, or just as adjuvant for oral hygiene. Compositions according to the invention comprise the glycolipid extract from *Oscillator Planktothrix* sp., preferably in amounts comprised between 0.1 and 100 µg/ml, more preferably in amounts comprised between 1 and 50 µg/ml or even more preferably comprised between 4 and 20 µg/ml, in general, for preparations for professional dental treatment, and ranging from 1 to 5 µg/ml for protective preparations for oral hygiene. Moreover, in one preferred aspect, these compositions comprise excipients, diluents and/or other active ingredients suitable for use in the oral cavity, such as for example: bacteriostatic or germicidal agents, e.g. quaternary ammonium derivatives (such as cetylpyridinium chloride or chlorhexidine, or surfactants, detergents, triclosan and similar compounds, e.g. DDDE (2,2,-dihydroxy-5.5 dibromodifenil ether) and stabilizers. As antibacterial agents it is also possible to use antibiotics, such as for example penicillin, erythromycin or tetracycline or other drugs with anti-bacterial activity. The compositions of the invention may also comprise known adjuvants of oral hygiene such as anti-tartar compounds like polyphosphates, anti-cavity agents like fluoride salts (e.g. monofluorophosphate), antiplaque compounds (such as urea, calcium lactate or similar), potassium salts as desensitizing agents (e.g. potassium citrate or similar).

The glycolipid extract can be diluted both in water and in a aprotic solvent such as DMSO and is stable in aqueous solution even when it is combined, for example, with chlorhexidine; moreover, it is also heat stable. In the formulation as mouth wash, the cyanobacterial extract is in aqueous solution or can be diluted in water, while in the solid compositions (toothpaste, gel, etc. candies or chewing gum) it may contain thickening or gelifying agents such as natural or synthetic polysaccharides (e.g. carrageen, carboxymethyl cellulose, hydroxymethyl cellulose, dextran, starch, vegetable glycerine), amorphous silica or titanium dioxide, natural or synthetic rubber (e.g. arabic gum) polyvinylpyrrolidone, polyethylene-glycol or compounds capable of conferring similar characteristics which are well known to the expert in the field. According to a further aspect the invention relates to a process for preparing the glycolipid fraction from a culture of *Oscillator Planktothrix* sp. as described by Yi et al. (11): the sample is treated at room temperature, comprised between 18 and 30° C., for a short incubation time of at least 5 minutes, preferably at least 10 minutes, including additional purification steps such as precipitation of at least the glycolipid fraction in the presence of sodium acetate and acetone, after extraction with a reagent based on: an organic solvent, preferably phenol, a chaotropic agent (such as guanidine thiocyanate) like Trireagent® (Sigma cat. N T3934) or similar reagents such as Trizol® (Invitrogen) and a second organic solvent such as chloroform, subsequent washes with 70% ethanol and removal of protein contaminants by digestion with a proteinase, for example proteinase K. These additional treatments allow to achieve a better specific activity since they result in removal of contaminants, such as phospholipids and heterologous proteins, that may have a stimulating effect on the production of pro-inflammatory cytokines, thus making the extract less effective. A reduced concentration of contaminants allows to use lower concentrations of crude extract in the oral cavity. Moreover, precipitation with salt (e.g. sodium acetate) and an organic solvent such as acetone, and further washes of the pellet with ethanol diluted in water, allow to eliminate residual traces of toxic solvents required to extract this kind of cellular constituents. According to a preferred embodiment, the process for *Oscillator Planktothrix* sp. extract preparation provides for a centrifugation of the cyanobacterial culture that has reached the stationary growth phase, in medium such as BG11 (Sigma-Aldrich cat. No. C3061), as described in Pomati et al (12). The so obtained pellet can be frozen prior to the extraction process which involves, after thawing:

a) pellet dilution, preferably with an equal volume of water or aqueous solvent, b) mixing with an appropriate volume of extraction solution (denaturant) described in (13), preferably consisting of a reagent based on a polar protic organic solvent, preferably phenol, and a chaotropic agent (such as guanidine thiocyanate) like Trireagent® (Sigma cat. N T3934) or similar reagents such as Trizol® (Invitrogen) and an organic aprotic solvent, such as chloroform, in a proportion of about 1 volume of aqueous suspension of cyanobacteria, 2-4 volumes of extraction solution, preferably about 3, and chloroform, about 0.5-1 volume;

c) incubation of the mixture for at least 5 minutes, more preferably for at least 10 minutes at room temperature;

d) centrifugation, preferably at about 2000×g and collection of the supernatant (aqueous phase) containing the glycolipid fraction, which can be measured by biochemical assay e.g. by electrophoresis and silver-staining, or by inhibition of cytotoxicity assay in the presence of LPS.

The cyanobacterial lysate obtained in d), which is the pellet obtained by centrifugation, can be optionally re-extracted to obtain the glycolipid fraction by re-addition of water or of aqueous buffer (in an amount approximately equal to the amount removed) and re-centrifugation of the sample. The second supernatant is pooled with the previous supernatant and then subjected to the following further steps:

e) precipitation by addition of salt, e.g. sodium acetate (5-20 mM final), and of an organic solvent, preferably acetone, in an amount equal to about 2 volumes, followed by centrifugation under the same conditions as above;

f) washing at least once, preferably twice, the pellet obtained by centrifugation with water-diluted ethanol, e.g. 70% ethanol, and resuspension of the pellet in an aqueous solution, preferably a buffered aqueous solution, e.g. TRIS 50 mM, g) enzymatic treatment of nucleic acid contaminants with endo- and exo-nucleases (for example DNAse and RNAse) and subsequent treatment of protein contaminants with a protease, for example proteinase K, preferably in an amount equal to 100 µg/ml, for a sufficient time (at least 1 hour at 37° C.). After enzymatic digestion, the sample is again centrifuged, the supernatant is recovered and is further precipitated by addition of salt (e.g. sodium acetate, approximately 10 mM final) and of an appropriate volume (preferably 2 volumes) of acetone or other organic solvent. The sample is centrifuged again, and the pellet is resuspended in water or in aqueous solution and subjected to molecular sieving by use of a filter (or other suitable device) with a cut off of 30 kilodaltons, thus resulting in elimination of everything passes through the filter and leading to the recovery of the lipid fraction retained, together with water or buffered aqueous solution.

The activity of the so obtained glycolipid fraction is measured by biological tests based on inhibition of the pro-inflammatory activity induced by LPS (from *P. gingivalis* or *E. coli*) in cells that produce cytokines such as IL-6, IL-8 TNF-alpha and/or IL-1β, as for example THP1, and/or by biochemical assays, as for example electrophoresis.

It is understood that the process described above can be modified by the person skilled in the art with small variations in e.g. the final concentrations and/or volumes and/or centrifugation conditions, without changing the activity of the final product.

According to a further aspect, the invention relates to a process for purification of the glycolipid fraction described in 10) which includes only step g) described above.

The steps removing traces of organic solvents, e.g. phenol, and the removal of most protein contaminants are important for applications to the oral cavity.

Indeed, the glycolipid extract obtained as described above shows a protein contamination <2% and a nucleic acid contamination <5%, according to measurement of the former by the Bradford method for protein assay and of the latter by spectrophotometric reading at 260 nm for nucleic acid determination.

According to a preferred aspect, the invention relates to a method for the prevention and treatment of gum disease, ranging from the milder form, such as gingivitis, to the most severe forms, such as periodontitis (pyorrhea) in all their respective stages, including also the chronic form, in the subjects affected by these disorders. The method consists in the treatment of the oral cavity with one of the compositions of the invention, by applying paste or gels to the site of infection or by using consistently the protective measures for oral hygiene according to the invention.

Furthermore, as mentioned above, since the anti-proinflammatory activity of the compositions of the invention is carried on after eradication of the bacterial agent, we consider the present invention both as treatment and prophylaxis, because inflammation of the gums or of dental sockets in the most severe forms of pyorrhea has consequences at the level of the dental sites—consisting primarily in the formation of periodontal pockets—which, in turn, facilitate bacterial colonization, the recurrence of infection and chronicization of the disease.

Moreover, as it is evident from the experimental data presented, the crude extract does not only antagonize the pro-inflammatory stimulus (consisting in the specific case of the LPS from *P. gingivalis*) when it is administered along with it, but also when it is administered before or after it (up to at least 4 hours later). For treatment and/or prevention it is meant both the professional treatment by a dentist, for example cleaning of periodontal pockets, and the maintenance of a better oral hygiene by use of the devices of the invention: toothpaste, gels, mouthwash, candies or chewing gum, with any of the compositions and devices of the invention.

The present invention also includes the cosmetic use of the compositions described, for treatment of gingival redness in mild cases of gingivitis.

EXPERIMENTAL PART

Example 1

Preparation of the Extract from *Oscillatoria Planktothrix* Fp1 Cultures

The extract was prepared from the cyanobacterium *Oscillatoria Planktothrix* FP1 (12) by adaptation to the current needs of the method for cold extraction of lipopolysaccharides (LPS), that was used so far only for LPS extraction from gram-negative bacteria, as described in Yi et al. In detail, cyanobacteria (CCAP 2 No. 1459/45, 9 Jul. 2008, Scotland UK) were diluted 1:1 in water, mixed with 3 volumes (where the volume unit is the total volume of cyanobacteria diluted in water) of Tri-reagent (Sigma-Aldrich cat. N. T3934) and 1 volume of chloroform and incubated for 10 minutes at room temperature.

At the end of incubation, centrifugation was performed at 2000×g for 15 min and the supernatant (aqueous phase) containing the active fraction was collected and evaluated by polyacrylamide gel electrophoresis followed by silver staining. This was followed by a further extraction from cyanobacteria, by re-addition of water (in an amount equal to the amount removed) and sample re-centrifugation. The so collected supernatants were precipitated with sodium acetate (10 mM final), 2 volumes of acetone and centrifuged. At the end of centrifugation, the supernatant was removed and the pellet was further washed twice with 70% ethanol. Subsequently the washing step supernatant was removed and the pellet was dissolved in 50 mm TRIS solution for RNAse and DNase digestion, followed by digestion with proteinase K (100 µg/ml) during overnight incubation at 37° C. The next day the sample was centrifuged at 2000×g for 15 min; the supernatant was recovered and precipitated in sodium acetate (10 mm final) and 2 volumes of acetone. The so obtained pellet was resuspended in water and passed through a filter with a cut-off of 30 KD, thus eliminating all the components with lower molecular weight.

The retentate was re-diluted in a suitable volume of water in order to obtain a concentration of the glycolipid fraction of at least 1 mg/ml for subsequent biological tests. The so obtained extract showed a protein contamination <2% and a nucleic acid contamination <5%.

Example 2

Inhibition of the Production of Pro-Inflammatory Cytokines Induced by P. gingivalis LPS The glycolipid fraction from *Oscillatoria Planktothrix* FP1, prepared as described in the previous example, was used to study in vitro the effects on the production of pro-inflammatory cytokines in a human monocytic cell line (THP1). The monocytes were brought to a concentration of $0.5 \times 10^6$ cells/ml, seeded in 24-well plates (1 ml/well) and incubated with LPS from *P. gingivalis* at a concentration of 1 µg/ml in the absence or presence of the cyanobacterial extract at various concentrations (1-20 µg/ml). Cultures were also made only in the presence of cyanobacterial extract at a concentration of 10 µg/ml. Cultures were incubated at 37° C. in a humidified incubator with 5% CO2 for 18-20 hours. After incubation, supernatants were collected and pro-inflammatory cytokines were quantified by use of a sandwiched Diaclone ELISA Kit (human TNF-alpha ELISA kit cat. N.950.090.096, human IL-6 ELISA kit cat. N. 950.030.096, human IL-8 ELISA kit cat N. 850.050.096, human IL1-beta ELISA kit cat N.850.006.096) (5).

The results showed that the cyanobacterial extract is unable to induce the production of pro-inflammatory cytokines in THP-1 cells.

In the presence of 1 µg/ml ultrapure LPS from *P. gingivalis* (Invivogen LPS-PG) that stimulates production of cytokines in the monocytic line, the extract simultaneously added to the bacterial LPS significantly inhibits production of tumor necrosis factor alpha (TNF-alpha), interleukin 6 (IL-6), interleukin 1 beta (IL-1 beta), interleukin 8 (IL-8) in a dose/response dependent manner.

Considering as 100% the production of inflammatory cytokines induced by *P. gingivalis* LPS, the crude extract at a concentration of 1 µg/ml proved to be capable of inhibiting production of TNF-alpha by 90%±10, of IL-6 by 92%±5, of IL-8 by 75±10%, of IL-1 beta by 62±8% (percentages represent the average of data in triplicate).

At a concentration of 20 µg/ml the extract proved to be able to strongly inhibit production of the pro-inflammatory cytokines tested, in an interval between 95 and 100% (FIG. 1). At a concentration of 20 µg/ml, the extract proved to be able to exert its inhibitory effects even when it was added several hours after LPS of *P. gingivalis* (FIG. 1 panels 1-4, up to 4 hours later).

Example 3

Evaluation of Toxicity, Stability and Solubility of the Cyanobacterial Extract in Composite Mixtures Toxicity The *Oscillatoria Planktothrix* FP1 extract was tested both in different cell lines (THP1, RAW 264.7, SKMEL-28, HEY4, SHSY-5Y) and in mononuclear cells obtained from peripheral blood (PBMC, peripheral blood mononuclear cells) at concentrations comprised between 1 and 100 µg/ml and proved to be non-toxic even when it was used at the highest concentration (100 µg/ml).

Stability in Solution

The *Oscillatoria Planktothrix* FP1 extract prepared as described in example 1 was mixed with chlorhexidine digluconate in water for 30 min at room temperature; subsequently, after purification to remove chlorhexidine, its effectiveness on monocyte cell cultures was retested. The results show that the glycolipid extract retains its activity, as measured by the ability to inhibit production of TNF-alpha induced by LPS from *P. gingivalis*. Inhibitions were 95%, 96% and 99% in the presence of extract respectively at concentrations of 1, 2, 4 µg/ml, by analogy to those observed in the absence of chlorhexidine. Cell viability was checked in the same cultures at the end of the incubation time and proved to be 100% in all cultures.

Stability in a Solid Matrix

The *Oscillatoria Planktothrix* FP1 extract was embedded in a hydroxyethyl cellulose matrix and, after one month, was tested for biological activity. Also in this case, the results showed that the glycolipid extract retains its biological activity with a degree of inhibition equal to 90%, 93% and 96%, respectively, at concentrations of 1, 2, 4 µg/ml, without affecting cell viability.

Heat Stability

The *Oscillatoria Planktothrix* FP1 extract prepared as described in Example 1, and dissolved in water, was brought to 100° C. for 5 min and subsequently tested for biological activity. Even in this case, the results showed that the glycolipid extract retains inhibitory activity on the production of TNF-alpha induced by *P. gingivalis* LPS without affecting cell viability.

Solubility

The *Oscillatoria Planktothrix* FP1 extract prepared in example 1 was dissolved in water at various concentrations up to 100 times higher than the optimal concentration tested in the experiment described in example 2.

Table 1 presents the data for solubility in water and dimethylsulfoxide (DMSO).

TABLE 1 solubility of the glycolipid extract

| Extract concentration | SOLVENT | |
| --- | --- | --- |
| | WATER | DMSO |
| 1 mg/ml | + | + |
| 2 mg/ml | + | + |
| 4 mg/ml | + | nd |
| 8 mg/ml | + | nd |

REFERENCES

1. Teng Y-T A. 2006. Protective and destructive immunity in the periodontum: part 1—Innate and humoral immunity and the periodontum. J. Dent. Res. 85:198-208.
2. Bodet C, Chandad F, Grenier D. 2006. Inflammatory responses of a macrophage/epithelial cell co-culture model to mono and mixed infections with *Porphyromonas gingivalis, Treponema denticola*, and *Tannerella forsythia*. Microbes Infection 8:27-35.
3. Bodet C, Chandad F, Grenier D. 2005. *Porphyromonas gingivalis*-induced inflammatory mediator profile in an ex vivo human whole blood model. Clin. Exp. Immunol. 143:50-57.

4. Wang P-L, Ohura K. 2002. *Porphyromonas gingivalis* lipopolysaccharide signaling in gingival fibroblasts-CD14 and toll-like receptors. Crit. Rev. Oral. Biol. Med. 13:132:142.
5. Shapira L, Champagne C, Van Dyke T E, Amar S. 1998. Strain-dependent action of monocytes and inflammatory macrophages by lipopolysaccharide of *Porphyromonas gingivalis*. Infect. Immunity 66:2736-2742.
6. Saba J A, McComb M E, Potts D L, Costello C E, Amar S. 2007. Proteomic mapping of stimulus-specific signalling pathways involved in THP-1 cells exposed to *Porphyromonas gingivalis* or its purified components. J. Proteome Res. 6:2211-2221.
7. Werts C, et al. 2001. Leptospiral lipopolysaccharide activates cells through a TLR-2 dependent mechanism. Nature 2:346-352.
8. Darveau R P, et al. 2004. *Porphyromonas gingivalis* lipopolysaccharide contains multiple lipid A species that functionally interact with both toll-like receptors 2 and 4. Infect. Immunity 72:5041-5051.
9. Zhou Q, Amar S. 2007. Identification of signaling pathways in macrophage exposed to *Porphyromonas gingivalis* or to its purified cell wall components. J. Immunol. 179:7777-7790.
10. Macagno A., et al. 2006. A cyanobacterial LPS antagonist prevents endotoxin shock and blocks sustained TLR4 stimulation required for cytokine expression. J. Exp. Med. 203:1481-92.
11. Yi E C, Hackett M. 2000. Rapid isolation method for lipopolysaccharide and lipid A from gram-negative bacteria. Analyst 125:651-656.
12. Pomati et al., 2000. The freshwater *Cyanobacterium Planctothrix* SP. FP1: Molecular Identification and Detection of Paralytic Shellfish Poisoning Toxins J. Phycol, 36:553-562 (2000).
13. Chomczynski P. and Mackey "Modification of the trireagent procedure for isolation of RNA from polysaccharide- and proteoglycan-rich sources" 19: 924 (1995).

The invention claimed is:

1. An isolated glycolipid fraction from *Oscillatoria Planktothrix* sp. for treating and/or reducing the risk of developing one or more gingival pathologies have a bacterial aetiology, wherein the isolated glycolipid fraction is obtained by
   a) suspending a pellet of the *Oscillatoria Planktothrix* sp. cyanobacterium with an aqueous solution in a volumetric ratio;
   b) mixing the cyanobacterial suspension with a denaturing solution comprising: a caotropic agent, a erotic organic solvent and an aprotic organic solvent, in a volume ratio comprised from 1:2 to 1:4,
   c) incubating for a time lower than 60 minutes;
   d) centrifugating and collecting the supernatant;
   e) precipitating the glycolipid fraction by addition of: a salt and an organic solvent; washing the pellet with water-diluted ethanol;
   f) re-suspending the pellet in an aqueous solution;
   g) treating the solution with nucleases; then treating the solution with a protease;
   h) precipitating further the glycolipid fraction, by addition of: a salt and an organic solvent;
   i) optional washing the pellet as in step f); further re-suspending it in an aqueous, solution;
   j) molecularly separating the re-suspended solution with a 30 k Dalton cut-off device;
   k) recovering the glycolipid fraction retained by the molecular separation of step j) with an aqueous, buffered solution and evaluating the protein and nucleic acids contamination degree, and wherein said glycolipid fraction has a degree of protein contamination below or equal to 2% and a degree of nucleic acids contamination below or equal to 5% by weight within the total glycolipid fraction.

2. The isolated glycolipid fraction according to claim 1 wherein said bacterial aetiology is due to an aetiological agent selected from the group consisting of: *Actinobacillum actinomycetemconcomitans, Porphyromonas gingivalis, Tannerella forsythia, Treponema denticola*.

3. The isolated glycolipid fraction according to claim 1 wherein said bacterial aetiology is due to the aetiological agent *Porphyromonas gingivalis*.

4. The isolated glycolipid fraction according to claim 1 wherein said gingival pathology is selected from the group consisting of: gingivitis and periodontitis (pyhorrea).

5. A dental composition comprising an isolated glycolipid fraction from *Oscillatoria Planktothrix* sp., wherein the isolated glycolipid fraction is obtained by
   a) suspending a pellet of the *Oscillatoria Planktothrix* sp. cyanobacterium with an aqueous solution in a volumetric ratio;
   b) mixing the cyanobacterial suspension with a denaturing solution comprising: a caotropic agent, a protic organic solvent and an aprotic organic solvent, in a volume ratio comprised from 1:2 to 1:4,
   c) incubating for a time lower than 60 minutes;
   d) centrifugating and collecting the supernatant;
   e) precipitating the glycolipid fraction by addition of: a salt and an organic solvent; washing the pellet with water-diluted ethanol;
   f) re-suspending the pellet in an aqueous solution;
   g) treating the solution with nucleases; then treating the solution with a protease;
   h) precipitating further the glycolipid fraction, by addition of: a salt and an organic solvent;
   i) optional washing the pellet as in step f); further re-suspending it in an aqueous, solution;
   j) molecularly separating the re-suspended solution with a 30 k Dalton cut-off device;
   k) recovering the glycolipid fraction retained by the molecular separation of step j) with an aqueous, buffered solution and evaluating the protein and nucleic acids contamination degree, and wherein said dental composition has a degree of protein contamination below or equal to 2% and a degree of nucleic acids contamination below or equal to 5% and excipients and/or diluents, stabilizers and/or additives, compounds suitable for the oral administration, and optionally one or more different active principle.

6. The dental composition according to claim 5 wherein said glycolipid fraction is in a quantity comprised from 0.1 and 100 µg/ml.

7. The dental composition according to claim 5, wherein the composition is in the form of a mouthwash, a gel, dentistry paste, or a toothpaste.

8. The dental composition according to claim 5, wherein the composition is in the form of a candy, a tablet, a chewing-gum, or a pill.

9. The dental composition according to claim 5 wherein said glycolipid fraction is in a quantity comprised from 1 to 50 µg/ml.

10. The dental composition according to claim 5 wherein said glycolipid fraction is in a quantity comprised from 4 to 20 µg/ml.

11. The dental composition according to claim 5 wherein said glycolipid fraction is in a quantity comprised from 1 to 5 µg/ml.

12. An isolated glycolipid fraction from *Oscillatoria Planktothrix* sp. for the treatment of gingival pathologies having a bacterial aetiology, obtained by
- a) suspending a pellet of the *Oscillatoria Planktothrix* sp. cyanobacterium with an aqueous solution in a volumetric ratio;
- b) mixing the cyanobacterial suspension with a denaturing solution comprising: a caotropic agent, a erotic organic solvent and an aprotic organic solvent, in a volume ratio comprised from 1:2 to 1:4,
- c) incubating for a time lower than 60 minutes;
- d) centrifugating and collecting the supernatant;
- e) precipitating the glycolipid fraction by addition of: a salt and an organic solvent; washing the pellet with water-diluted ethanol;
- f) re-suspending the pellet in an aqueous solution;
- g) treating the solution with nucleases; then treating the solution with a protease;
- h) precipitating further the glycolipid fraction, by addition of: a salt and an organic solvent;
- i) optional washing the pellet as in step f); further re-suspending it in an aqueous, solution;
- j) molecularly separating the re-suspended solution with a 30 k Dalton cut-off device:
- k) recovering the glycolipid fraction retained by the molecular separation of step j) with an aqueous, buffered solution and evaluating the protein and nucleic acids contamination degree, wherein said glycolipid fraction has a degree of protein contamination below or equal to 2% and a degree of nucleic acids contamination below or equal to 5% by weight within the total glycolipid fraction.

13. A process for the preparation of a glycolipid fraction from *Oscillatoria Planktothrix* sp., having a degree of protein contamination below or equal to 2% and a degree of nucleic acids contamination below or equal to 5% consisting in the following steps:
- a) suspending a pellet of the *Oscillatoria Planktothrix* sp. cyanobacterium with an aqueous solution in a volumetric ratio;
- b) mixing the cyanobacterial suspension with a denaturing solution comprising: a caotropic agent, a protic organic solvent and an aprotic organic solvent, in a volume ratio comprised from 1:2 to 1:4,
- c) incubating for a time lower than 60 minutes;
- d) centrifugating and collecting the supernatant;
- e) precipitating the glycolipid fraction by addition of: a salt and an organic solvent; washing the pellet with water-diluted ethanol;
- f) re-suspending the pellet in an aqueous solution;
- g) treating the solution with nucleases; then treating the solution with a protease;
- h) precipitating further the glycolipid fraction, by addition of: a salt and an organic solvent;
- i) optional washing the pellet as in step f); further re-suspending it in an aqueous solution;
- j) molecularly separating the re-suspended solution with a 30 k Dalton cut-off device;
- k) recovering the glycolipid fraction retained by the molecular separation of step j) with an aqueous, buffered solution and evaluating the protein and nucleic acids contamination degree.

14. The process according to claim 13, wherein in the suspending step a) the volumetric ratio is comprised from 1:1 to 1:2.

15. The process according to claim 13, wherein in the mixing step b) the organic solvent is phenol, the aprotic organic solvent is chloroform, and they are in a volume ratio comprised from 1:2 to 1:4.

16. The process according to claim 13, wherein in the mixing step b) the organic solvent is phenol, the aprotic organic solvent is chloroform, and wherein the volume ratio of the organic solvent to the aprotic organic solvent is 1:3.

17. The process according to claim 13, wherein in steps a), f) and i) the pellet is re-suspended in an aqueous, buffered solution.

18. The process according to claim 13, wherein in step g) the solution is treated with endo- and/or exonucleases; and with proteinase K.

19. The process according to claim 13, wherein the organic solvent of steps e) and h) is acetone.

20. A method of treating a gingival pathology having a bacterial aetiology in an subject, comprising administering to the subject an effective amount of the glycolipid fraction from *Oscillatoria Planktothrix* sp. of claim 1.

* * * * *